United States Patent [19]

Coffen et al.

[11] Patent Number: 5,008,411
[45] Date of Patent: Apr. 16, 1991

[54] GLYCIDIC ACID ESTER AND PROCESS OF PREPARATION

[75] Inventors: David L. Coffen, Glen Ridge; Pradeep B. Madan, Edison; Alan Schwartz, Montclair, all of N.J.

[73] Assignee: Hoffmann-La Roche Inc., Nutley, N.J.

[21] Appl. No.: 416,295

[22] Filed: Oct. 2, 1989

Related U.S. Application Data

[63] Continuation-in-part of Ser. No. 197,934, May 24, 1988, abandoned.

[51] Int. Cl.$^5$ .................. C07D 306/13; C07D 301/02
[52] U.S. Cl. .................................... 549/519; 549/549; 540/491; 560/17; 435/156
[58] Field of Search ............................... 549/519, 549

[56] References Cited

U.S. PATENT DOCUMENTS

| | | | |
|---|---|---|---|
| 3,562,257 | 2/1971 | Kugita et al. | 540/491 |
| 4,471,130 | 11/1984 | Katsuki et al. | 549/523 |
| 4,552,695 | 11/1985 | Igarashi et al. | 540/491 |
| 4,590,188 | 5/1986 | Takeda et al. | 540/491 |
| 4,640,930 | 2/1987 | Mohacsi et al. | 540/491 |
| 4,652,561 | 3/1987 | Mohacsi et al. | 540/491 |
| 4,694,002 | 9/1987 | Floyd et al. | 540/491 |
| 4,864,058 | 9/1989 | Mohacsi | 490/491 |

FOREIGN PATENT DOCUMENTS

| | | | |
|---|---|---|---|
| 61-145159 | 7/1986 | Japan | 490/491 |
| 61-145160 | 7/1986 | Japan | 490/491 |
| 61-145173 | 7/1986 | Japan | 490/491 |
| 61-145174 | 7/1986 | Japan | 490/491 |
| 61-268663 | 11/1986 | Japan | 490/491 |

OTHER PUBLICATIONS

Laumen et al., J. Chem. Soc., pp. 148–150 (1989).
Whitesell et al., J. Org. Chem., vol. 50, pp. 4663–4664 (1985).
Whitesell et al., Chimia, vol. 40, pp. 318–321 (1986).
Sanada et al, "Chemical Abstracts", 108:131290r (1988).
Hayashi et al, "Chemical Abstracts", 106:326200u (1987).

Primary Examiner—Robert T. Bond
Attorney, Agent, or Firm—George M. Gould; Bernard S. Leon; George W. Johnston

[57] ABSTRACT

A process for the preparing a compound of the formula

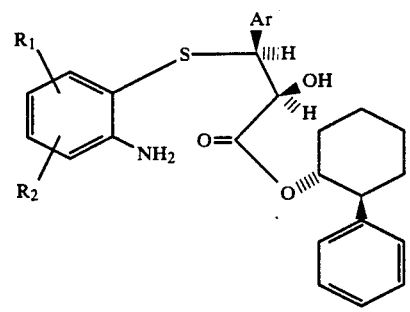

wherein $R_1$ and $R_2$ are each independently hydrogen, alkyl of 1 to 4 carbon atoms, alkoxy of 1 to 4 carbon atoms, halogen, trifluoromethyl or nitro; or $R_1$ and $R_2$ taken together with the benzene ring to which they are attached are naphthalene, and Ar is p-lower alkoxy phenyl.

which comprises reacting

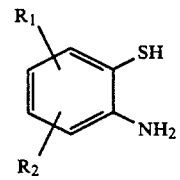

wherein $R_1$ and $R_2$ are as described above with the compound of the formula

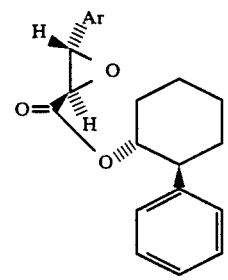

wherein Ar is as described above,
in an aromatic organic compound. The intermediates formed by the process of the invention are useful in the production of thiazepin-4(5H)-ones which have activity as calcium channel blockers and accordingly are useful as agents for lowering blood pressure and agents for treating ischemia.

5 Claims, No Drawings

GLYCIDIC ACID ESTER AND PROCESS OF PREPARATION

RELATED APPLICATION

This is a continuation-in-part of U.S. application Ser. No. 07/197,934, filed May 24, 1988, now abandoned.

BACKGROUND OF THE INVENTION

Diltiazem has the following chemical formula:

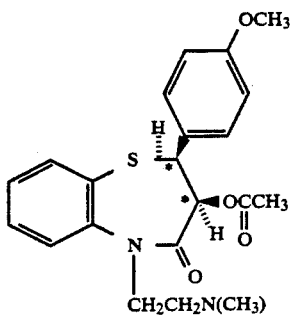

As can be seen, diltiazem has two asymmetric carbons at the starred positions. Because it has two asymmetric carbons, diltiazem is one of four possible stereoisomers.

Diltiazem is the most useful of the four stereoisomers, and as pictured above, it can be seen that it has the (2S, 3S) configuration at the two asymmetric positions.

Since diltiazem is one of four stereoisomers, in a non-stereospecific syntheses, the desired (2S, 3S) isomer can be obtained in at most a 25% yield.

Known processes for preparing diltiazem which fix the starred positions (the 2- and 3-positions) in the cis relative configuration at an intermediate stage, still prepare intermediates as optically inactive racemates. Accordingly, optical resolution, which can be expensive and time consuming, is still required at some point. Moreover, such optical resolutions can be best give a 50% yield of diltiazem.

BRIEF SUMMARY OF THE INVENTION

The process of the invention avoids the above-described time, expense, and inefficiency in the preparation of diltiazem. In fact, the process of the invention can be used in the preparation of all of the compounds of formula I

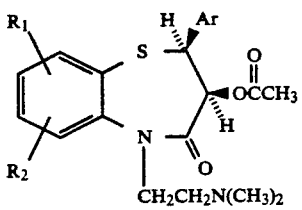

wherein $R_1$ and $R_2$ are each independently hydrogen, alkyl of 1 to 4 carbon atoms, alkoxy of 1 to 4 carbon atoms, halogen, trifluoromethyl or nitro; or $R_1$ and $R_2$ taken together with the benzene ring to which they are attached are naphthalene; and Ar is p-lower alkoxy phenyl.

All of the compounds of formula I, which encompasses diltiazem, have two asymmetric carbons of the (2S, 3S) configuration.

Compounds of formula I will be referred to herein as thiazepin-4(5H)-ones.

The invention relates to a process for the preparation of compounds of the formula:

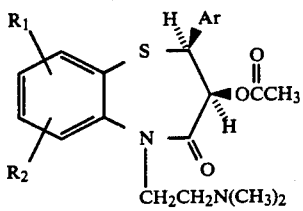

wherein $R_1$ and $R_2$ are each independently hydrogen, alkyl of 1 to 4 carbon atoms, alkoxy of 1 to 4 carbon atoms, halogen, trifluoromethyl or nitro; or $R_1$ and $R_2$ taken together with the benzene ring to which they are attached are naphthalene; and Ar is p-lower alkoxy phenyl.

The process comprises:

(a) reacting (−)-(1R,2S)-2-phenylcyclohexanol with chloroacetyl chloride to form (−)-(1R,2S)−2-phenylcyclohexyl chloroacetate of the formula

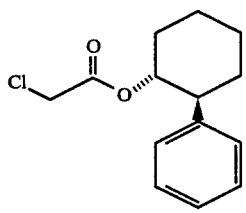

(b) reacting (−)-(1R,2S)-2-phenylcyclohexyl chloroacetate with an aldehyde of the formula

Ar—CHO wherein Ar is p-lower alkoxy phenyl; to form (2R,3S)-3-(aryl) oxirane carboxylic acid (1R,2S)-2-phenylcyclohexyl ester of the formula

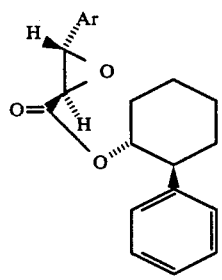

wherein Ar is as described above, (c) reacting (2R,3S)-3-(aryl)oxirane carboxylic acid (1R,2S)-2-phenylcyclohexyl ester with an o-aminoaryl-thiol to obtain a compound of the formula

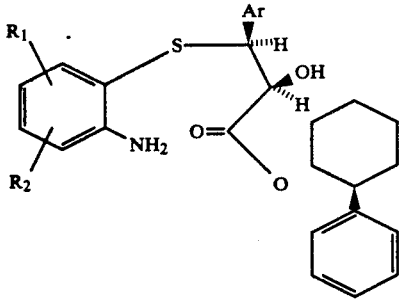

wherein $R_1$, $R_2$, and Ar are as described above, (d) hydrolyzing the product of step (c) to obtain a compound of the formula

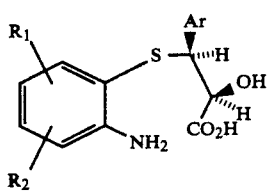

wherein $R_1$, $R_2$ and Ar are as described above, (e) cyclizing the product of step (d) to obtain a compound of the formula

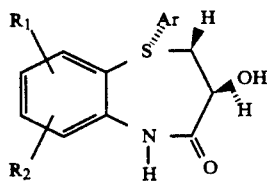

wherein $R_1$, $R_2$, and Ar are as described above, (f) reacting the product of step (e) with 2-dimethylaminoethylchloride to obtain a compound of the formula

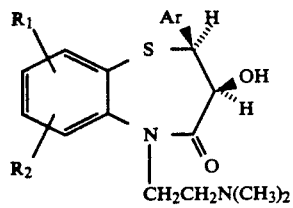

wherein $R_1$, $R_2$ and Ar are as described above.

Additionally, the product of step (f) can be acylated at the hydroxy group to achieve a compound of formula I.

Alternatively, the product of step (c) can be directly cyclized by heating in an organic solvent to obtain a hydrolyzed compound of formula

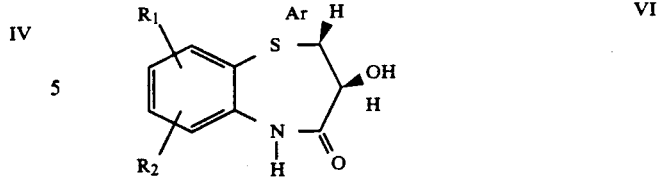

wherein $R_1$, $R_2$ and Ar are as described above, which can in turn be N-alkylated, and acylated to obtain a thiazepin-4(5H)-one.

In another aspect, the invention relates to intermediates of the formulas

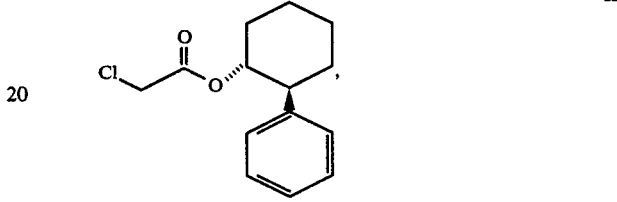

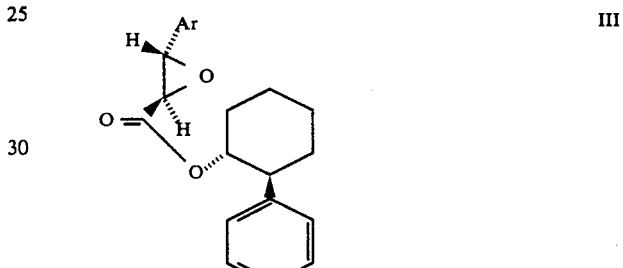

wherein Ar is p-lower alkoxy phenyl, and

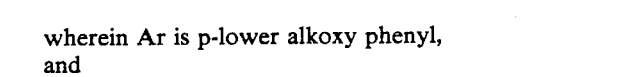

wherein $R_1$ and $R_2$ are each independently hydrogen, alkyl of 1 to 4 carbon atoms, alkoxy of 1 to 4 carbon atoms, halogen, trifluoromethyl or nitro; or $R_1$ and $R_2$ taken together with the benzene ring to which they are attached are naphthalene; and Ar is p-lower alkoxy phenyl.

Thiazepin 4(5H)-ones are calcium channel blockers and therefore are useful as agents in the treatment of high blood pressure and ischemia.

DETAILED DESCRIPTION OF THE INVENTION

As used herein, the term "lower alkyl" denotes a straight or branched-chain alkyl group containing 1 to 4 carbon atoms, for example, methyl, ethyl, propyl, isopropyl, butyl, and the like. Alternatively, the number of carbon atoms in an alkyl group is designated herein as in "alkyl of 1 to 4 carbon atoms" which denotes a straight or branched chain alkyl group containing 1 to 4 carbon atoms. The term "lower alkoxy" denotes a straight or branched-chain lower alkoxy group containing 1 to 4 carbon atoms, for example, methoxy, propoxy, isopropoxy, butoxy and the like. Alternatively, the number of carbon atoms in an alkoxy group is designated herein as in "alkoxy of 1 to 4 carbon atoms" which denotes a straight or branched chain alkoxy group of 1 to 4 carbon atoms. The term "halogen" denotes the halogens, that is, bromine, chlorine, fluorine, and iodine. The term "lower alkanoyloxy" denotes a straight or branched-chain alkanoyloxy group of 2 to 5 carbon atoms, for example, acetyloxy, propionyloxy, butyryloxy, and the like.

As used in the formulas herein a solid line (—) indicates a substituent that is above the plane of the page, a broken line (॥॥॥) indicates a substituent that is below the plane of the page.

As used herein, the term "cis" denotes a compound wherein $R_1$ and $R_2$ substituents are both on the same side of a ring.

The invention relates to a process for the preparation of compounds of the formula

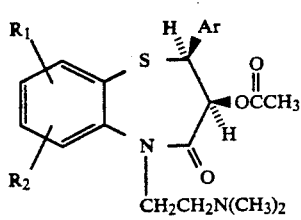
I wherein $R_1$ and $R_2$ are each independently hydrogen, alkyl of 1 to 4 carbon atoms, alkoxy of 1 to 4 carbon atoms, halogen, trifluoromethyl or nitro; or $R_1$ and $R_2$ taken together with the benzene ring to which they are attached are naphthalene; and Ar is p-lower alkoxy phenyl.

The process comprises reacting (—)-(1R,2S)-2-phenyl cyclohexanol of the formula

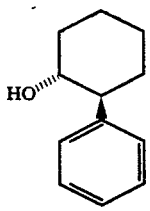
VIII with chloroacetyl chloride to obtain a compound of the formula

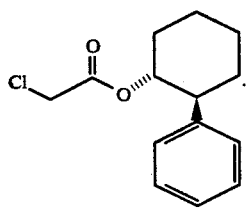
II

The reaction is conducted in a basic organic solvent such as a mixture of pyridine and methylene chloride or more preferably a mixture of 4-dimethylaminopyridine and methylene chloride at reflux. The compound of the formula VIII is known and can be prepared as described in the examples herein.

In the next step, a compound of formula II is reacted with an aldehyde of the formula Ar—CHO wherein Ar is p-lower alkoxy phenyl, to yield a mixture of compounds of the formulas

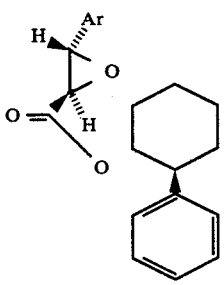
III

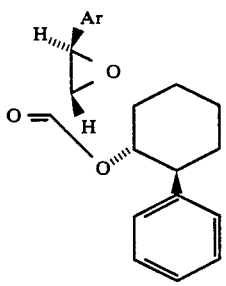
IX wherein Ar is as described above.
Aldehydes of the formula

Ar—CHO wherein Ar is as described above, are known or can be prepared in accordance with known methods.

The reaction is conducted in the presence of a basic reagent such as sodium hydride in a polar aprotic solvent such as ether, or more preferably, tetrahydrofuran into which can be mixed a non-polar organic solvent such as pentane or hexane. The reaction is conducted under an inert atmosphere such as nitrogen, or more preferably argon. The reaction is conducted at room temperature but because it is exothermic it proceeds to higher temperatures, such as, for example about 55° C.

The desired stereoisomer of formula III from the above reaction mixture which is, (2R,3S)-3-aryloxirane carboxylic acid (1R,2S)-2-phenylcyclohexyl ester, may be separated from the undesired stereoisomer of formula IX by conventional means. In a most preferred embodiment of the invention, wherein Ar is 4-methoxyphenyl, the desired stereoisomer of formula III, (2R,3S)-3-(4-methoxyphenyl)oxirane carboxylic acid (1R,2S)-2-phenylcyclohexyl ester crystallizes from a hexane ethyl acetate solvent mixture while the corresponding undesired stereoisomer of formula IX remains in solution, so that the desired stereoisomer of formula III may be separated by fractional crystallization.

(2R,3S)-3-aryloxirane carboxylic acid (1R,2S)-2-phenylcyclohexyl ester, is reacted with a thiol of the formula

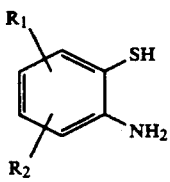

wherein R₁ and R₂ are as described above; preferably in an organic solvent such as benzene, or more preferably toluene, at about the reflux temperature of the solvent for about 1 day to obtain an ester of the formula

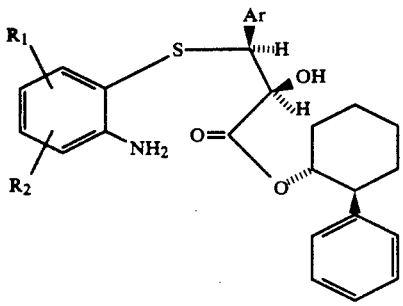

wherein $R_1$, $R_2$ and Ar are as described above.

Thiols of formula X are known or can be prepared in accordance with known procedures.

An ester of formula IV is reacted with a base such as potassium hydroxide or more preferably sodium hydroxide in a polar, protic solvent such as methanol or more preferably ethanol with argon or more preferably nitrogen being bubbled through the reaction mixture, at about the reflux temperature of the solvent for about 1 to 10 hours and then further at room temperature for about 12 hours to obtain an acid of the formula

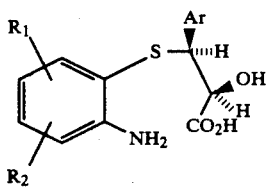

wherein $R_1$, $R_2$ and Ar are as described above.

An acid of formula V is reacted, preferably in an organic solvent such as benzene, toluene, or more preferably a mixture of xylenes at about the reflux temperature of the solvent, for about 5 to about 30 hours, with nitrogen being bubbled through the reaction mixture, and in the presence of an organic acid catalyst such as p-toluenesulfonic acid. monohydrate to obtain the cyclized compound of formula

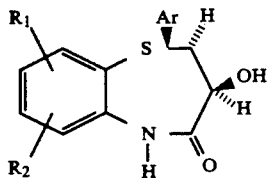

wherein $R_1$, $R_2$ and Ar are as described above.

Alternatively, a compound of formula IV may be directly cyclized to a compound of formula VI without isolation of an intermediate compound of formula V.

In the next step, a compound of formula VI is reacted with a compound of formula $$ZCH_2CH_2N(CH_3)_2 \qquad XI$$

wherein Z is halogen, preferably chloride. The reaction is carried out by reacting an alkali metal salt of a compound of formula VI such as the sodium or more preferably potassium salt thereof with an amino alkyl halide of formula XI preferably the chloride thereof, in a polar organic solvent such as, methyl acetate, or more preferably ethyl acetate, at about 40° C. to about 80° C., or at the reflux temperature of the solvent employed, which in the case of ethyl acetate is 77° C., for a period of about 10 to about 30 hours.

The reaction is carried out in the presence of a base, such as potassium hydroxide or more preferably potassium carbonate in acetone, or in a lower alkyl acetate. Separation of the product of this reaction which is a compound of formula

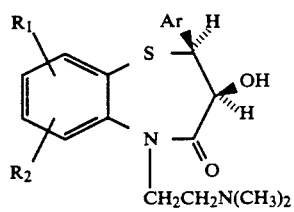

wherein $R_1$, $R_2$ and Ar are as described above, can be by conventional means such as crystallization.

Alternatively, a compound of formula VI may be reacted with a different amino alkyl halide so as to obtain compounds with amino alkyl side chains as in U.S. Pat. Nos. 4,652,561 and 4,694,002 which are hereby incorporated by reference.

A compound of formula VII can be acylated by reaction with acetic anhydride, or acetyl bromide or chloride optionally in the presence of a base such as pyridine, triethylamine, or dimethylaniline at room temperature or up to about 115° C., to obtain a compound of formula

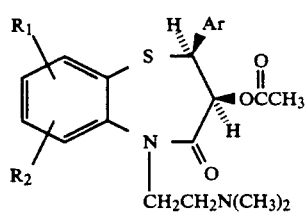

wherein $R_1$, $R_2$ and Ar are as described above.

It can be seen from the above synthetic scheme, that the synthesis involves the use of a chiral auxiliary of the formula II
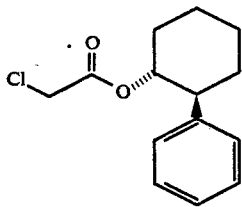

to obtain an intermediate having the proper stereochemistry, of the formula

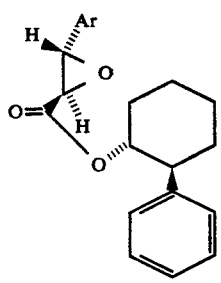
III wherein Ar is described above,
which in turn is condensed with a thiol of formula X to yield the compound of formula

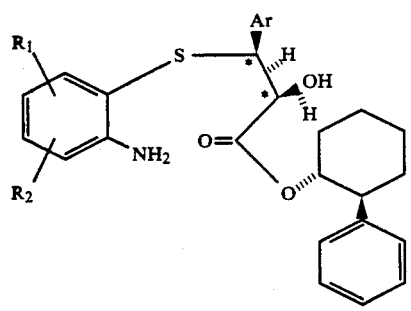
IV wherein $R_1$, $R_2$ and Ar are as described above and wherein the two carbons at the starred positions have the proper stereochemistry. The sterically pure epoxide of formula III causes the condensed compound of formula IV to have the proper stereochemistry at the starred positions.

Preparation of the optically active alcohol of formula VIII which serves as the chiral auxiliary is disclosed in J. K. Whitesell and R. M. Lawrence, Chimia 318, 1986 which is hereby incorporated by reference. Phenylmagnesium bromide in the presence of copper chloride is reacted at about $-40$ to about $-10°$ C. with cyclohexene oxide. The reaction is conducted by adding the cyclohexene oxide dropwise to a solution of phenylmagnesium bromide in ether or more preferably tetrahydrofuran to which copper chloride has been added. The resulting ($\pm$)-trans-2-phenylcyclohexanol can be isolated by conventional means such as extraction and crystallization.

In the next step, ($\pm$)-trans-2-phenylcyclohexanol is reacted with chloroacetyl chloride at reflux in a basic solvent such as a mixture of methylene chloride and pyridine or, more preferably, 4-dimethylaminopyridine and methylene chloride. The resulting ($\pm$)-trans-2-phenylcyclohexyl chloroacetate of the formula

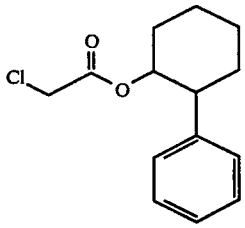
VIII' can be isolated by conventional means such as extraction followed by distillation of the organic layer.

In the next step, which is another aspect of this invention, ($\pm$)-trans-2-phenylcyclohexyl chloroacetate in deionized water at a pH of about 7.5 has added to it a catalytic amount of a lipase in portions over about a half hour to 5 hours. The lipase used can be selected from several available hydrolytic enzymes of this class.

Preferably a microbial lipase is employed and most preferably the lipase from Pseudomonas fluorescens, also known as P-30 Amano is employed. A base, such as potassium hydroxide, or more preferably sodium hydroxide is then added. The resulting compound ($-$)-(1R,2S)-2-phenylcyclohexanol of the formula

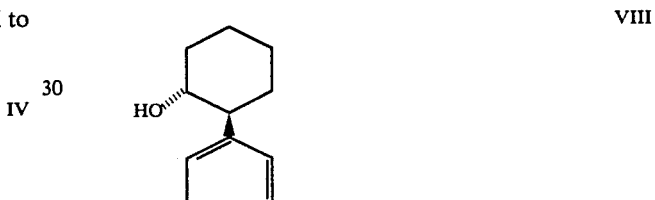
VIII is recovered by extraction with methylene chloride followed by fractional crystallization from petroleum ether.

Preferred final products of the process of the invention are thiazepin-4(5H)-ones of the formula

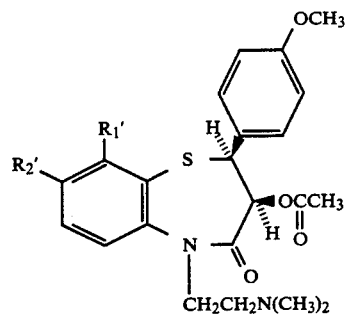
I' wherein $R_1$ is hydrogen or chlorine, and $R_2$ is hydrogen; or $R_1$ and $R_2$ taken together with the benzene ring to which they are attached are naphthalene.

A preferred final product of the process of the invention is (+)-(2S,3S)-2-(4-methoxyphenyl)-3-acetyloxy-5-[2-(dimethylamino)ethyl ]9-chloro-2,3dihydro-1,5-benzothizaepin-4-(5H)-one.

A more preferred final product of the process of the invention is (+)-(2S,3S)-2-(4-methoxyphenyl)-3-acetyloxy-5-[2-(dimethylamino)ethyl]-2,3-dihydro-1,5-benzothiazepin-4-(5H)-one.

A most preferred final product of the process of the invention is (+)-(2S,3S)-(3-acetyloxy)-2,3-dihydro-2-(4- methoxyphenyl)-5-[2-(dimethylamino)ethyl]naphtho[1,2-b][1,4]thiazepin-4(5H)-one.

The final products of the process of the invention, that is thiazepin-4(5H)-ones of formula I, have activity as calcium channel blockers and accordingly are useful as agents for lowering blood pressure and as agents for treating ischemia. There are distinct advantages to the process of the invention as compared for example to the process for producing naltiazem which is (+)-(2S,3S)-(3-acetyloxy)-2,3-dihydro-2-(4-methoxyphenyl)-5-[2-(dimethylamino)ethyl]naphtho[1,2-b][1,4]thiazepin-4(5H)-one which is described in U.S. Pat. No. 4,652,561, and which involves resolution of a cyclized compound of the formula More specifically, the present process does not require chromatography, or resolution of any intermediates, and produces naltiazem with a purity equivalent to the process of U.S. Pat. No. 4,652,561, which involves resolution of the just above mentioned compound using tartaric acid. Moreover, because the proper stereochemistry is induced at the positions marked by stars in the compound of the formula

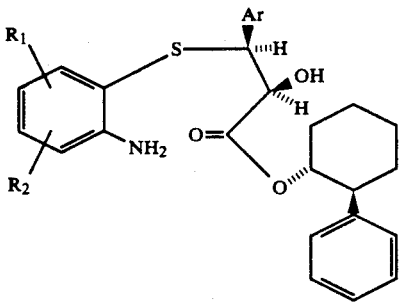

wherein $R_1$, $R_2$ and Ar are as described above, by the addition of the optically active epoxide and a thiol rather than by a resolution after the thiol adduct is prepared, less of the commercially unavailable thiols are required to produce a given amount of naltiazem. Moreover, the chiral auxiliary (−)-(1R,2S)-2-phenylcyclohexanol which is split off after condensation of the optically active epoxide and the thiol can easily be recovered for future use as follows.

After isolation of a compound of formula V, or VI, the mother liquors can be evaporated to yield (−)-(1R,2S)-2-phenylcyclohexanol.

(−)-(1R,2S)-2-phenylcyclohexanol can also be obtained from the undesired epoxide of formula

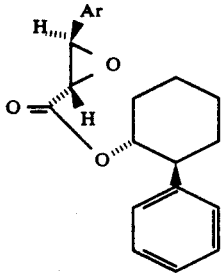

wherein Ar is as described above
by dissolving it by heating on a steam bath in methanol, or more preferably ethanol. Then aqueous base such as aqueous potassium hydroxide, or more preferably aqueous sodium hydroxide is added. The resulting chiral auxiliary (−)-(1R,2S)-2-phenylcyclohexanol can be recovered by conventional means such as extraction followed by The examples which follow further illustrate the invention. All temperatures are in degrees Celsius unless otherwise stated.

EXAMPLE 1

Preparation of (±)-Trans-2-Phenylcyclohexanol

A 50-L reactor equipped with a stirrer, a gas bubbler, and an addition funnel was placed under argon, charged with 27.36 L (27.63 mole) of phenylmagnesium bromide (1.0 M), which is known, in tetrahydrofuran and cooled to 15° C. whereupon 235 g (2.37 mole) of CuCl was added. The resulting mixture was further cooled to −25° C. To this well-stirred mixture was added dropwise over 1.0 hour 1.82 L (18.0 mole, 1766g) of cyclohexene oxide, which is known. After the addition was completed, the mixture was stirred between −10° C. and 0° C. for 4 hours. The reaction mixture was subsequently quenched with 6 L of saturated $NH_4SO_4$ solution followed by 4L of water. The organic layer was separated and the aqueous layer was then extracted with 3×6L=18 L of ethyl acetate. The combined organic layers were evaporated in vacuo. When the residue was dissolved into 8 L of methylene chloride, a small aqueous layer separated and was discarded. The organic layer was dried ($Na_2SO_4$) and evaporated in vacuo, finally at 0.5 mmHg. The residue on crystallization from hexane, afforded in 3 crops, 2.96 kg (93%) of (±)-trans-2-phenylcyclohexanol as colorless needles, m.p. 55-57° C.

Anal. Calcd for $C_{12}H_{16}O$: C, 81.76; H, 9.16. Found: C, 81.54; H, 9.15.

EXAMPLE 2

Preparation of (±)-Trans-2-Phenylcyclohexyl Chloroacetate

A mixture of 2.17 k9 (12.3 mole) of (±)-trans-2-phenylcyclohexanol, 1475 mL (18.43 mole) of chloroacetyl chloride, 6 g (0.049 mole) of 4-dimethylaminopyridine, and 5.5 L of methylene chloride was heated at reflux. After 8 hours, thin layer chromatography analysis (4:1 hexane-ethyl acetate: Spray 5% $NH_4MoO_4$ in 10% aqueous $H_2SO_4$) indicated complete reaction. The reaction mixture was allowed to cool to room temperature and was stirred with 2×4 L=8 L of saturated $NaHC_{O3}$. The organic layer was dried ($Na_2SO_4$) evaporated in vacuo on a rotary evaporator, and finally at 0.5 mmHg to afford 3.21 kg of crude (±)-trans-2-phenylcyclohexyl chloroacetate. Distillation of the tan liquid afforded 2.76 kg (88%) of the desired product as a colorless liquid, (b.p. 125-133°/0.3-0.5 mmHg). The chloroacetylation of other lots of (±)-trans-2-phenylcyclohexanol was accomplished in ←95%. The particular lot of (±) alcohol used in this example was only about 91% pure.

EXAMPLE 3

Enzymatic (Lipase from Pseudomonas Fluorescens) Kinetic Resolution of (±)-Trans-2-Phenylcyclohexyl Chloroacetate and Isolation of (−)-(1R,2S)-2-phenylcyclohexanol 101 g (0.40 mole) of (=)-2-phenylcyclohexyl chloroacetate was poured into a 500-mL multi-neck flask equipped with a mechanical stirrer, pH probe (connected to a pH controller) and base inlet (connected to a peristaltic pump controlled by the pH controller). A solution of 10 mL of pH=7 buffer and 90 mL of deionized water was added to the flask and the mixture was rapidly stirred and heated to 45–50° C. (by an oil bath). The pH was adjusted to pH=7.5 and when a steady pH was achieved, the mixture was ready for enzyme addition. 2.0 g of Lipase P-30 Amano was added in two portions to the rapidly stirring mixture over 2 hours. Immediately, 1N NaOH addition began at a constant rate from a reservoir connected to one inlet of the peristaltic pump. After about 48 hours, 180 mL (90% of theory) of 1N NaOH had been added. After another 16 hours a total of 188 mL (94% of theory) of 1N NaOH had been added. The mixture was cooled to room temperature and was extracted with 2×400 mL =800 mL of $CH_2Cl_2$ which was dried and concentrated to an oil, (84.3 g) and fractionally crystallized from 150 mL of petroleum ether (30–60° C.) at −10° C. for 3 hours to give 24.5 g (34.8%) of (−)-(1R,2S)-2-phenylcyclohexanol as colorless needles, m.p. 63–64° C., $[\alpha]_D^{25}=-57.3°(c=1; MeOH)$.

Anal. Calcd for $C_{12}H_{16}O$: C, 81.76; H, 9.16. Found: C, 81.81 H, 9.36.

The mother liquors were concentrated to an oil, taken up in 100 mL of petroleum ether (30–60° C.), poured onto 80 g of dry silica (230–400 mesh) and eluted with 1 L of hexanes. Evaporation of the solvent gave 48.0 g of the (+) enriched chloroacetate. The plug was washed with 400 mL of ethyl acetate. After evaporation the residue was suspended in 30 mL of petroleum ether (30–60° C.) at −10° C. to give 6.8 g of (−)-(1R,2S)-2-phenylcyclohexanol, m.p. 64–65° C., $[\alpha]_D^{20}=-58.1°(c=1; MeOH)$. The total 31.3 g represents 44% (89% of theoretical) yield.

EXAMPLE 4

Preparation of (−)-(1R, 2S)-2-Phenylcyclohexyl Chloroacetate

A mixture of 790 g (4.48 mole) of pure (−)-(1R,2S)-2-phenylcyclohexanol, 1.5 L of methylene chloride, 450 mL (5.625 mole) of chloroacetyl chloride, and 2.2 g (0.96 mole) of 4-dimethylaminopyridine was heated at reflux for 8 hours. On cooling, the reaction mixture was stirred with 2 ×1.5 L=3.0 L of saturated $NaHCO_3$ for 30 minutes. The organic layer was dried ($Na_2SO_4$) and evaporated to dryness, finally at 0.5 mm for 4 hours to afford 1.136 kg of the title compound (100%) as an oil.

Anal. Calcd for $C_{14}H_{17}ClO_2$: C, 66.53; H, 6.78; Cl, 14.03. Found: C, 66.69; H, 6.79; Cl, 14.27.

EXAMPLE 5

Preparation of (2R,3S)-3-(4-Methoxyphenyl)oxirane Carboxylic Acid (1R,2S)-2-Phenylcyclohexyl Ester A 5.0-L three-necked flask equipped with a stirrer, a gas bubbler, a thermometer, an addition funnel and condenser was charged with 100 g (3.33 mole) of NaH (80% in mineral oil), and triturated with 3×500 mL=1.5 L of hexane. Each portion of hexane was decanted when the NaH had settled. Under an argon atmosphere, 1.5 L of tetrahydrofuran was added followed by a solution of 568 g (2.247 mole) of (−)-(1R,2S)-2-phenylcyclohexyl chloroacetate, 352 g (2.589 mole) of anisaldehyde and 250 mL of tetrahydrofuran over 0.5 hour via addition funnel. A vigorous evolution of $H_2$ gas ensued along with an exotherm to about 55°. After the initial reaction subsided, the mixture was then stirred under argon at ambient temperature overnight. The mixture was heated at 55–60° for 1 hour and then quenched into 8.0 L of ice water. The pH was adjusted to 7 with 390 mL of 3N $H_2SO_4$ and the resulting mixture was extracted first with 4 L followed by 2×2 L for a total of 8.0 L of methylene chloride. The combined organic layers were dried ($Na_2SO_4$) and evaporated in vacuo to an oily, partially solid residue which on crystallization from 0.5 L of (9:1) hexanes-ethyl acetate afforded colorless needles. These crystals were collected by filtration, washed with 2×200 mL=400 mL of 9:1 hexanes-ethyl acetate followed by 2×500 mL=1.0 L of cold hexanes and finally dried in vacuo to afford 403 g (51%) of the title compound, m.p. 146–148° C., $[\alpha]_D^{20}=-146°(c=1; CHCl_3)$.

Anal. Calcd for $C_{22}H_{24}O_4$: C, 74.97; H, 6.86. Found: C, 74.80; H, 6.88.

EXAMPLE 6

Preparation of (2S,3S)-3-[(2-Amino-1-naphthalene)thio]-2-hydroxy-3-(4-methoxyphenyl)Propanoic Acid (1R,2S)-2-Phenylcyclohexyl Ester Hydrochloride A mixture of 409.5 g (1.162 mole) of (2R,3S)-3-(4-methoxyphenyl)oxirane carboxylic acid (1R,2S)-2-phenylcyclohexyl ester, 221 g (1.26 mole) of 2-aminonaphthalene-1-thiol and 2.2 L of toluene was stirred and heated at reflux under argon for 20 hours, cooled to about 50° and then treated with 240 mL (1.16 mole) of HCl (gas) in ethyl acetate (4.83 molar). Solids began to form and the mixture was diluted with 500 mL of acetonitrile and stirred for 1 hour. The precipitated solids were collected by filtration, washed first with 3×500 mL=1.5 L of acetonitrile, then with 500 mL of ether, and dried at 70° in vacuo overnight to afford 645 g (98%) of the title compound as a light yellow solid, m.p. 184–186°, $[\alpha]_D^{20}=+52°(c=0.1; acetone)$.

Anal Calcd for $C_{22}H_{33}NO_4S.HCl$: C, 68.13; H, 6.07; N, 2.48. Found: C, 68.85; H, 6.09; N, 2.63.

EXAMPLE 7

Preparation of (+)-(2S,3S)-3-[2-Amino-1-naphthalene)thio]-2-hydroxy-3-(4-methoxyphenyl) propanoic acid A 1-L three-necked flask equipped with magnetic stir bar, condenser and nitrogen bubbler was charged with 66.6 g (0.11081 mole) of (2S,3S)-3-[(2-amino-1-naphthalenyl) thio]-2-hydroxy-3-(4-methoxyphenyl)-propanoic acid (1R,2S)-2-phenylcyclohexyl ester hydrochloride and then 350 mL of ethanol was added to create a slurry of solids. Then after 124 mL (0.25 mole) of 2N NaOH was added, the mixture was refluxed for 4 hours and then stirred at room temperature overnight. The reaction mixture was extracted with 3×500 mL=1500 mL of ether to remove (−)-(1R,2S)-2-phenylcyclohexanol. The aqueous layer was acidified to pH=3 with 3N $H_2SO_4$, then 100 mL of acetonitrile was added and the mixture was stirred overnight. THe pH was then 5–6, therefore the PH was adjusted to 3 with 3N $H_2SO_4$ and allowed to stir another 24 hours whereupon the heterogeneous mixture (pH=3) was filtered and dried overnight under vacuum to yield 41.2 g (94.5%), m.p. 174–177° C. decomposition, $[\alpha]_D^{20}=+288°(c=0.5; MeOH)$.

EXAMPLE 8

Preparation of
(2S,3S)-2,3-Dihydro-3-hydroxy-2-(4-methoxyphenyl)-naphtho-[1,2-b]-1,4-thiazepin-4(5H)-one via Cyclization of
(+)-(2S,2S)-3-[2-amino-1-naphthalenyl)thio]-2-hydroxy-3-(4-methoxyphenyl) Propanoic Acid A 2-L round-bottomed flask equipped with a magnetic stir-bar, a Dean-Stark trap, a condenser, and a nitrogen bubbler was charged with 41.0 g (0.111 mole) of (+)-(2S,3S)-3-[2-amino-1-naphthalenyl)thio]-2-hydroxy-3-(4-methoxyphenyl)propanoic acid. This material was suspended in 1.34 L of xylenes. After adding 4.0 g (0.02 mole) of p-toluenesulfonic acid.monohydrate, the mixture was refluxed for 19 hours. Upon cooling to room temperature, the precipitated solids were filtered out and washed first with 100 mL of ethyl acetate and then with 500 mL of ether. After air drying, the yield of fluffy, white crystalline (2S,3S)-2,3-dihydro-3-hydroxy-2-(4-methoxyphenyl)naphtho[1,2-b][1,4]thiazepin-4(5H)-one was 33.0 g (85%), m.p. 243–245° C., $[\alpha]_D^{20} = +24.2°(c=0.5;$ acetone).

EXAMPLE 9

Preparation of
(2S,3S)-2.3-Dihydro-3-hydroxy-2-(4-methoxyphenyl)-naphtho-[1,2-b]-1,4-thiazepin-4(5H)-one via Cyclization of
(2S,3S)-3-[(2-amino-1-naphthalenyl)thio]-2-hydroxy-3-(4-methoxyphenyl)propanoic acid (1R,2S)-2-phenylcyclohexyl ester)

A 10-gallon extractor was charged with 12.0 L of 3N Na$_2$CO$_3$, 575 g (1.02 mole) of (2S,3S)-3-[(2-amino-1-naphthalenyl)thio]-2-hydroxy-3-(4-methoxyphenyl) propanoic acid (1R,2S)-2-phenylcyclohexyl ester hydrochloride and 8.0 L of methylene chloride. The aqueous layer was successively extracted with an additional 4L+2L=6.0 L of methylene chloride. The combined organic layers were dried by filtration through a pad of anhydrous potassium carbonate and evaporated in vacuo to afford the free base which was taken up in 11.5 L of xylene. Then 16 g of p-toluene sulfonic acid.-monohydrate was added and this mixture was stirred at reflux under argon for 16 hours (overnight). After cooling, the product was collected by filtration, washed with 500 mL of ethyl acetate, followed by 3×500 mL =1.5 L of ether and air dried overnight to afford 318 g (89%) of (2S,3S)-2,3-dihydro-3-hydroxy-2-(4-methoxyphenyl)-naphtho-[1,2-b][1,4]thiazepin-4(5H)-one as colorless needles, m.p. 235–238° decomposition, $[\alpha]_D^{20} = +24.87°(c=0.4;$ acetone).

EXAMPLE 10

Preparation of
(+)-(2S,3S)-2,3-Dihydro-3-hydroxy-2-(4-methoxyphenyl)-5-[2-dimethylamino)ethyl]naphtho[1,2-b][1,4]thiazepin-4(5H)-one A 1-L three-necked flask equipped with a mechanical stirrer and a reflux condenser open to the atmosphere was charged with 25.0 g (0.071 mole) of (2S,3S)-2,3-dihydro-3-hydroxy-2-(4-methoxyphenyl)-naphtho-[1,2-b][1,4]thiazepin-4(5H)-one 20.5 g (0.141 mole) of 2-dimethylaminoethyl chloride.hydrochloride 40 g (0.29 mole) of finely pulverized anhydrous K$_2$CO$_3$, 3 mL of water, 500 mL of ethyl acetate, and the whole heterogeneous mixture was refluxed with a steam bath for 16 hours. Thin layer chromatography analysis (8:1, CH$_2$Cl$_2$:MeOH) showed the reaction was complete and therefore while warm, the mixture was filtered and washed with 2×50 mL=100 mL of ethyl acetate. The combined organic filtrate was concentrated to near dryness and the resultant crystals were collected by vacuum filtration and washed with 3×50 mL=150 mL of ether. The solids were air-dried to give 25.6 g (85%) of the title compound as a white solid, m.p. 153–154° C., $[\alpha]_D^{20} = +44°(c=5;$ MeOH). A second crop of the title compound as tan crystals 1.1 g (3.6%) was obtained by concentration of the mother liquors and trituration with ethyl acetate, m.p. 149–153° C., $[\alpha]_D^{20} = +41.2°(c=.5;$ MeOH).

EXAMPLE 11

Preparation of
(+)-(2S,3S)-(Acetyloxy)-2,3-dihydro-2-(4-methoxyphenyl)-5-[2-(dimethylamino)ethyl]naphtho[1,2-B][1,4]thiazepin-4(5H)-one A 500-mL flask equipped with a magnetic stir bar and a nitrogen bubbler was charged with 25.0 g (0.059 mole) of (+)-(2S,3S)-2,3-dihydro-3-hydroxy-2-(4-methoxyphenyl)-5-[2-dimethylamino)ethyl]naphtho[1,2-b][1,4]thiazepin-4(5H)-one, 250 mL of CH$_2$Cl$_2$, 0.25 g (0.002 mole) of 4-dimethylaminopyridine, 4.8 g (.145 mole) of acetic anhydride and the homogeneous mixture was allowed to stir overnight. Thin layer chromatographic analysis (1:1 ethyl acetate:methanol) showed the reaction to be complete and therefore 200 g of ice-water was added to the mixture producing a milky, opaque mixture. The layers were separated, the CH$_2$Cl$_2$ layer was washed with 150 mL of 5:1 H$_2$O:NH$_4$OH solution and the layers were allowed to separate in a separatory funnel. The organic layer was placed on a rotary evaporator and concentrated to a foam, 29.5 g. Because of polar impurities, the oil was dissolved into 150 mL of ether, applied to a 50 g plug of silica, the plug was washed first with 500 mL of ether and then 2×150 mL of ethyl acetate. The fractions were free of polar impurities and combined and concentrated to an oil, 29.0 g. The oil was dissolved into 100 mL of ethyl acetate and then 20 mL of 4.8M HCl in EtOAc was added dropwise over 15 minutes. Then 25 mL of ether was added immediately causing a solid mass to precipitate. The mixture was heated on a steam bath until solution occurred and then solids began to precipitate slowly on cooling. The solid title compound, 19.1g, was off-white, m.p. 229–230° C., $[\alpha]_D^{20} = +218°(c=0.65;$ MeOH; 316 nm Hg lamp).

The mother liquors were concentrated to give 8.1 g, m.p. 129–130° C. of a pure white solid, $[\alpha]_D^{20} = +214.6°(c=0.5;$ MeOH; 316 nm Hg lamp). A third crop of 1.0 g of tan solid was obtained (m.p. 225–230°). The total yield obtained was 95%.

EXAMPLE 12

Preparation of
(2S,3S)-3-(2-Aminophenyl)thio-2-hydroxy3-(4-methoxybenzene) Propanoic Acid (1R, 2S)-2-Phenylcyclohexyl Ester A mixture of 352.4 g (1.0 mole) of (2R,3S)-3-(4-methoxyphenyl)oxirane carboxylic acid (1R,2S)-2-phenylcyclohexyl ester 1.41 L of toluene and 123 mL (1.14 mole) of 2-aminobenzene thiol was stirred at reflux under argon for 16 hours (overnight). Thin layer chromatography (7:3 hexanes:EtOAc; short wave UV) indicated that the reaction was complete. The reaction mixture was evaporated in vacuo to dryness. The residue, on crystallization from ethanol afforded on cooling, 297 g (62.2%) of the title compound as colorless needles, m.p 131–133°. An additional 9.5g, m.p. 129–131° C. was obtained for a total of 65%. On a 25 g scale a 81% yield was obtained.

Anal. Calcd for $C_{28}H_{31}NO_4S$: C, 70.41; H, 6.54; N, 2.93. Found: C, 70.34 H, 6.56; N, 3.02.

EXAMPLE 13

Preparation of (2S,3S)-3-(2-Aminophenyl)thio-2-hydroxy-3-4-methoxybenzene Propanoic Acid A mixture of 24 g (0.05 mole) of (2S,3S)-3-(2-aminophenyl)thio-2-hydroxy-3-(4-methoxybenzene)-propanoic acid (1R,2S)-2-phenylcyclohexyl ester, 100 mL (0.20 mole) of 2N sodium hydroxide, and 200 mL of ethanol was stirred at reflux under argon for 2 hours (thin layer chromatography indicated complete reaction). The mixture was evaporated in vacuo to a volume of about 100 mL, diluted with 50 mL of water and extracted with 2×250 mL=500 mL of ether to remove (1R,2S)-2-phenylcyclohexanol. The aqueous layer was acidified with 3N $H_2SO_4$ to pH4, extracted into 2×150 mL=300 mL of methylene chloride dried ($Na_2SO_4$) and evaporated in vacuo. The residue, on trituration with acetonitrile afforded in two crops, 13.0 g (81%) of the title compound as a light yellow solid, m.p. 138–140°, $[\alpha]_D^{20}=+357.1°(C=0.3; EtOH)$.

Anal. Calcd for $C_{16}H_{17}NO_4S$ : C, 60.17; H, 5.36; N, 4.38. Found: C, 59.16 H, 5.21; N, 4.54.

EXAMPLE 14

Preparation of (+)-(2S,3S)-2.3-Dihydro-3-hydroxy-2-(4-methoxyphenyl)-1,5-benzothiazepin-4(5H)-one A. From (2S,3S)-3-(2-Aminophenyl)thio-2-hydroxy-3-(4-methoxybenzene) Propanoic Acid (1R,2)2-phenylcyclohexyl ester A mixture of 351 g (0.7349 mole) of (2S,3S)-3-(2-aminophenyl)thio-2-hydroxy-3-(4-methoxybenzene) propanoic acid (1R,2S)-2-phenylcyclohexyl ester, 10.5 g of p-toluenesulfonic acid.monohydrate and 6.0 L of xylenes was stirred at reflux under argon using a Dean-Stark apparatus for 16 hours. Thin layer chromatography (1:1 hexanes:EtOAc; short wave UV) indicated a complete reaction and the mixture was then cooled to 5° using an ice-bath. The precipitated solids were collected by filtration, and washed with 2×250 mL=500 mL of hexanes to afford 162 g (73.2%) of (+)-(2S,3S)-2,3-dihydro-3-hydroxy-2-(4-methoxyphenyl) -5-benzothiazepin-4(5H)-one as a light yellow solid, m.p. 203–205°, $[\alpha]_D^{20}=+107.9°$ (C=0.3; EtOH).

Anal. Calcd for $C_{16}H_{15}NO_3S$: C, 63.76; H, 5.02; N, 4.65; S, 10.64. Found; C, 63.65; H, 4.97; N, 4.53; S, 10.37.

B. From (2S,3S)-3-(2-aminophenyl)thio-2-hydroxy-3-4-methoxybenzene propanoic acid A mixture of 13 g (0.0407 mole) of (2S,3S)-3-(2-aminophenyl)thio-2-hydroxy-3-(4-methoxybenzene) propanoic acid, 0.4 g of p-toluene sulfonic acid.monohydrate and 125 mL of xylenes was stirred at reflux under argon using a Dean-Stark apparatus for 16 hours (overnight). Thin layer chromatography (1:1 hexanes:EtOAc; short wave UV) indicated that the reaction was complete. On cooling, the precipitated solids were collected by filtration, and washed with hexane to afford 10.8 g (88%) of (+)-(2S,3S)-2,3-dihydro-3-hydroxy-2-(4-methoxyphenyl)-1,5-benzothiazepin-4(5H) -one as a colorless solid, m.p. 201–203°, $[\alpha]_D^{20}=+124.1°(C=.3; EtOH)$.

EXAMPLE 15

Preparation of (+)-(2S,3S)-5-[2-Dimethylamino)ethyl]-2,3-Dihydro-3-hydroxy-2-(4-methoxyphenyl)-1,5-benzothizaepin-4(5H) -one A 5-L three-necked flask equipped with a heating mantle, a mechanical stirrer and a condenser was charged with 162 g (0.54 mol) of (+)-(2S,3S)-2,3-dihydro-3-hydroxy-2-(4-methoxyphenyl)-1,5-benzothiazepin-4(5H)-one and then 1 L of ethyl acetate. After stirring to dissolve the solution, 100 g (0.694 mol) of dimethylaminoethyl chloride.HCl was added in one portion followed by 300 g (2.16 mol) of finely ground $K_2CO_3$ and 5 mL of $H_2O$. (The 5 ml. of water was essential to cause a reaction between the phases, while addition of much more water would have resulted in gummy mixture that was difficult to filter.) This heterogeneous mixture was rapidly stirred at reflux for 5 hours. By thin layer chromatography (8:1, $CH_2Cl_2$-MeOH, short wave UV), reaction was complete and therefore the mixture was allowed to cool to room temperature, filtered through a sintered glass funnel and washed with 100 mL 1:1 hexanes-ethyl acetate. The solvent was evaporated and on standing the oil crystallized. Recrystallization from ether gave 140 g (70%) of colorless crystalline (+)-(2S,3S)-5-[2-(dimethylamino)ethyl]-2,3-dihydro-3-hydroxy-2-(4-methoxyphenyl)-1,5-benzothiazepin-4(5H)-one, m.p. 79–81° C., $[\alpha]_D^{20}=+156.4°(C=1.0; CHCl_3)$.

Anal. Calcd for $C_{20}H_{24}N_2O_3S$: C, 64.50; H, 6.50; N, 7.52; S, 8.59. Found; C, 64.83; H, 6.63; N, 7.28; S, 8.40.

The residual mother liquor contained more (+)-(2S,3S)-5-[2-(dimethylamino)ethyl]-2,3-dihydro-3-hydroxy-2-(4-methoxyphenyl)-1,5-benzothiazepin-4(5H)-one by thin layer chromatography but would not crystallize. This material was acylated separately to diltiazem.HCl ); by isolation of this final product it can be determined that at least 36.5 g (18.2%) additional (+)-(2S,3S)-5-[2-(dimethylamino)ethyl]2,3-dihydro-3-hydroxy-2-(p-methoxyphenyl)-1,5-benzothiazepin4(5H)-one was contained in these mother liquors. The total yield was therefore 88.2%.

EXAMPLE 16

Preparation of (+)-(2S,3S)-3-(Acetyloxy)-2,3-Dihydro-5-[2(dimethylamino)ethyl]-2-(4-methoxyphenyl)-1,5-benzothiazepin-4(5H)-one.HCl(Diltiazem Hydrochloride)

A mixture of 118 g (0.3168 mole) of (+)-(2S,3S)-5-[2-(dimethylamino)ethyl]-2,3-dihydro-3-hydroxy-2-(p-methoxyphenyl)-1,5-benzothiazepin-4(5H)-one, 375 mL of methylene chloride, 1.85 g of 4-dimethylaminopyridine, and 50 mL of acetic anhydride was heated at reflux under argon for 3 hours. Thin layer chromatography (1:1 EtOAc-MeOH, short wave UV) indicated complete reaction. The mixture was poured into 500 mL of ice-water and 100 mL of brine was added. The organic layer was separated and aqueous layer was extracted with an additional 250 mL of methylene chloride. The combined organic layers were washed with 800 mL of 5:1 NH₄OH—H₂O and the aqueous layer was back-extracted with 200 mL of methylene chloride. The combined methylene chloride layers were dried (Na₂SO₄) and evaporated in vacuo to dryness. The residue was dissolved in 250 mL of methanol and treated with anhydrous HCl (gas) to a PH of 2. To the resulting solution was added 350 mL of ether. The precipitated solids were collected by filtration and washed with 10% methanol-ether to afford 131.5 g (92%), after reacylation, of diltiazem hydrochloride as a colorless solid, m.p. 208–210°. $[\alpha]_D^{20} = +98.8°(C=1; MeOH)$.

Anal. Calcd for C₂₂H₂₆N₂O₄S·HCl: C, 58.59; H, 5.80; N, 6.21; S, 7.10. Found; C, 58.22; H, 6.05; N, 6.13; S, 6.93.

We claim:

1. A process for preparing the compound of the formula

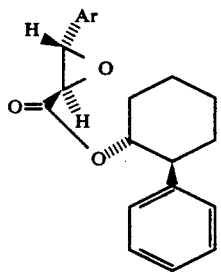

wherein Ar is p-lower alkoxy phenyl, which comprises reacting the compound of formula

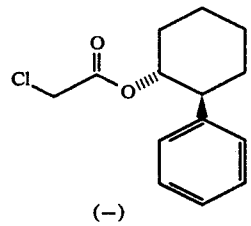

with the compound of formula

Ar—CHO wherein Ar is as described above, in a solvent in the presence of a basic reagent.

2. A process according to claim 1, wherein the solvent is tetrahydrofuran.

3. A process according to claim 1, wherein the basic reagent is sodium hydride.

4. A substantially optically pure compound of the formula

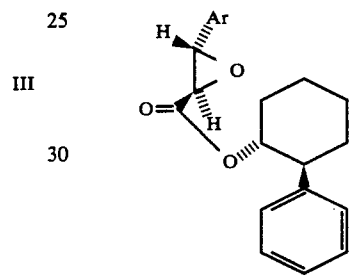

wherein Ar is p-lower alkoxy phenyl.

5. A compound in accordance with claim 4, (2R,3S)-3-(4-methoxyphenyl)oxirane carboxylic acid (1R,2S)-2-phenylcyclohexyl ester.

* * * * *